(12) United States Patent
Gomm et al.

(10) Patent No.: US 6,487,916 B1
(45) Date of Patent: Dec. 3, 2002

(54) ULTRASONIC FLOW METERING SYSTEM

(75) Inventors: Tyler J. Gomm, Meridian, ID (US);
Nancy C. Kraft, Idaho Falls, ID (US);
Jason A. Mauseth, Pocatello, ID (US);
Larry D. Phelps, Pocatello, ID (US);
Steven C. Taylor, Idaho Falls, ID (US)

(73) Assignee: Bechtel BXWT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/496,787

(22) Filed: Feb. 2, 2000

(51) Int. Cl.[7] ............................................. G01F 1/66
(52) U.S. Cl. .......................... 73/861.29; 73/861.28; 73/861.27
(58) Field of Search ......................... 73/861–861.94, 73/196

(56) References Cited

U.S. PATENT DOCUMENTS

| | | | |
|---|---|---|---|
| 3,575,050 A | | 4/1971 | Lynnworth .................... 73/194 |
| 3,653,259 A | * | 4/1972 | McShane ................. 73/861.27 |
| 3,697,936 A | | 10/1972 | Zacharias, Jr. et al. ......... 340/3 |
| 3,779,070 A | * | 12/1973 | Cushman et al. .......... 73/865.5 |
| 3,818,757 A | * | 6/1974 | Brown .................... 73/861.28 |
| 3,834,806 A | | 9/1974 | Whited .......................... 355/3 |
| 3,881,352 A | * | 5/1975 | Mcshane ................. 73/861.23 |
| 3,914,998 A | * | 10/1975 | Mcshane ................. 73/861.28 |
| 3,974,693 A | * | 8/1976 | Hardies .................... 73/861.28 |
| 3,981,176 A | | 9/1976 | Jacobs ............................ 73/24 |
| 4,003,242 A | | 1/1977 | Houben et al. ................. 73/24 |
| 4,011,755 A | | 3/1977 | Pedersen et al. .............. 73/194 |
| 4,095,457 A | | 6/1978 | Koda et al. ..................... 73/53 |
| 4,313,343 A | | 2/1982 | Kobayashi et al. ........... 73/290 |
| 4,331,025 A | | 5/1982 | Ord, Jr. ........................... 73/54 |
| 4,442,719 A | * | 4/1984 | Allen et al. ............... 73/861.29 |
| 4,555,932 A | | 12/1985 | Crosby, Jr. ...................... 73/24 |
| 4,576,047 A | | 3/1986 | Lauer et al. ................... 73/597 |
| 4,596,133 A | | 6/1986 | Smalling et al. ................ 73/24 |
| 4,656,864 A | | 4/1987 | Kraus et al. .................... 73/24 |
| 4,662,212 A | | 5/1987 | Noguchi et al. ................ 73/24 |
| 4,691,557 A | * | 9/1987 | Dunn et al. ................. 73/32 A |
| 4,724,812 A | | 2/1988 | Akagi ......................... 123/435 |
| 5,060,514 A | | 10/1991 | Alysworth .................. 73/24.01 |
| 5,285,675 A | | 2/1994 | Colgate et al. .............. 73/23.2 |
| 5,285,677 A | | 2/1994 | Gehler ....................... 73/24.01 |
| 5,313,820 A | | 5/1994 | Aylsworth .................. 73/24.01 |
| 5,325,703 A | | 7/1994 | Magori ....................... 73/23.32 |
| 5,343,760 A | | 9/1994 | Sultan et al. ............. 73/861.04 |
| 5,351,522 A | | 10/1994 | Lurat ......................... 73/24.01 |
| 5,353,627 A | | 10/1994 | Diatschenko et al. ...... 73/19.03 |
| 5,369,979 A | | 12/1994 | Aylsworth et al. ......... 73/24.01 |
| 5,392,635 A | | 2/1995 | Cadet et al. ................ 73/24.01 |
| 5,467,637 A | | 11/1995 | Hasegawa et al. ......... 73/24.01 |
| 5,537,854 A | | 7/1996 | Phillips et al. ............. 73/24.01 |
| 5,546,813 A | | 8/1996 | Hastings et al. .......... 73/861.29 |
| 5,627,323 A | | 5/1997 | Stern ......................... 73/861.28 |
| 5,796,009 A | * | 8/1998 | Delsing .................... 73/861.28 |
| 6,204,344 B1 | * | 3/2001 | Kendrick et al. .............. 526/64 |

* cited by examiner

*Primary Examiner*—Benjamin R. Fuller
*Assistant Examiner*—Andre Allen
(74) *Attorney, Agent, or Firm*—Workman Nydegger & Seeley

(57) ABSTRACT

A system for determining the density, flow velocity, and mass flow of a fluid comprising at least one sing-around circuit that determines the velocity of a signal in the fluid and that is correlatable to a database for the fluid. A system for determining flow velocity uses two of the inventive circuits with directional transmitters and receivers, one of which is set at an angle to the direction of flow that is different from the others.

60 Claims, 8 Drawing Sheets

ULTRASONIC FLOW METERING SYSTEM

RELATED APPLICATION

This application claims priority from provisional application Ser. No. 60/118,563 filed Feb. 4, 1999.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention

BACKGROUND OF THE INVENTION

1. Field of the Invention

The present invention relates to a system for metering flow velocity. More particularly, the present invention relates to a system that measures acoustic pulses in a flowing fluid. In particular, the present invention relates to a velocimeter and a method of comparing acoustic transmission delays between at least two velicometers.

2. Relevant Technology

Many fluid flow applications require real-time evaluation for various reasons such as fluid quality evaluation and process control. Such real-time evaluation allows for dynamic control and monitoring of the fluid flow application. The evaluation of fluid flow in a conduit may be due to the need to control, monitor, or adjust the dynamic volume of fluid being delivered through the conduit. Measuring the flow in a conduit is useful in a number of applications.

One such application is measuring the flow of water through an irrigation pipe, particularly in commercial irrigation applications. Flow measurement is useful for several reasons, including the ability to track the amount of water delivered to a portion of land in order to provide adequate irrigation. Additionally, where irrigation is used, water needs to be employed efficiently. For such reasons, irrigation systems require the ability to monitor the volumetric delivery of water and to measure flow rate.

Another application is measuring the flow of natural gas through a pipe, particularly as it is delivered from the gas fields to metropolitan areas. Measuring both the flow and the concentration of gas is useful for several reasons including the ability to track the total amount of gas being delivered from the gas fields as a response to consumer demand.

Closer to the end use, the monitoring of natural gas as it is mixed with ambient air and charged to a combustion device, may be critical for proper operation of the device. As gas flow meters typically measure a pressure drop such as by using the Venturi principle, the pressure drop may adversely affect the combustion device.

A number of devices for measuring flow rate exist for various applications. The size of the conduit being used, accuracy, cost, and other factors may play a role in determining what type of measuring device will be used for a specific application. One flow metering system uses differential pressures that are detectable with pressure transducers. Measuring flow in this manner requires the conduit to contract. Typical systems for contracting the flow profile include installing a section of pipe which tapers to a significantly smaller diameter.

The contraction of the flow of water through an irrigation pipe is undesirable for a number of reasons. For example, irrigation water often contains debris which can cause an obstruction in a small diameter pipe or which can become caught against a restriction. An obstruction will result in plugging of the pipe, requiring time, energy, and expense to unplug or otherwise repair it. In addition, time required to reverse plugging may jeopardize crops which go unwatered during unscheduled down time.

Another problem with differential pressure producing devices is that there is often significant retrofitting required to incorporate them into the system where flow is being measured. For example, in the case of devices which use a gradual reduction in the diameter of the conduit, a relatively long section of conduit must be removed and replaced with a tapering conduit section.

Another problem with measuring flow in a conduit is that variations in temperature and humidity can adversely affect detection conditions. These are often the types of conditions of commercial irrigation applications. More pronounced is the effect of temperature and humidity variations upon gaseous flow due to the tendency of the gas to expand or contract, and to change in quality where humidity is different between the gas source and the delivery point.

Another approach to measuring flow rate is the so-called elbow flow meter in which a curved section of pipe in the fluid delivery system is fitted with pressure sensors to measure pressure differential in the elbow. In order to measure the flow accurately, the sensors must be precisely placed in both the outer and inner circumferential walls of the elbow, in the same radial plane, and then must be calibrated.

The elbow flow meter itself, however, presents problems of its own. Initially, the mere fact that an elbow must be put into a pipe requires designing the pipe with a bend therein, or removing a section of the pipe to put a first elbow that diverts the flow direction, and a second elbow that restores the flow direction. The elbow flow meter may be configured with pressure transducers that measure the pressure of the fluid both before and after the elbow.

One problem occurs where transducers are located at different elevational levels, particularly for liquids, such that a slight pressure measurement bias is introduced due to the elevation difference. An elevation difference therefore requires calibration of the pressure transducers. Two or more transducers may be placed at each location both above and below the elbow but this requires averaging of the pressure measurements and a single malfunctioning pressure transducer will give a spurious average.

Another problem with elbow flow meters is the disturbance caused by the elbow bend itself that creates eddies, and other turbulence that may cause a spurious pressure reading downstream from the bend. As such, under certain flow regimes such as the laminar flow- to the laminar-to-turbulent-transition region, the disturbance at the bend may require the downstream transducer to be placed at a significant distance, thus complicating configuration of the flow meter. Additionally, where flow velocity variations may vary significantly between laminar and fully turbulent flow, the placement of a downstream transducer at a single location will be inadequate to monitor pressure drop for all flow regimes.

What is needed in the art is a fluid flow meter that avoids the problems of the prior art. Additionally, what is needed in the art is a fluid flow meter that does not require the obstruction or constriction of the flow in the conduit. What is also needed in the art is a fluid flow meter that does not require redirecting the flow of the fluids such as with an elbow and the like.

Such systems, methods, and apparatuses are disclosed and claimed herein.

SUMMARY AND OBJECTS OF THE INVENTION

The present invention relates to a system for measuring fluid flow that avoids the problems of the prior art. The inventive system uses a plurality of "sing-around" circuits that may filter out capacitive couplings for gaseous systems and that filter out electronic noise for fluid systems in general.

The inventive system uses at least two non-intrusive sing-around circuits that send an audio signal through the flowing fluid within a conduit. A first sing-around circuit sends an audio signal in a direction perpendicular to the flow of the fluid. A second sing-around circuit sends an audio signal in a direction that is oblique to the direction of flow of the fluid in the conduit. Although such variables as fluid density, fluid temperature, fluid pressure, and fluid velocity must be monitored during ordinary metering of fluid flow, the inventive combination of the two sing-around circuits eliminates the need to monitor fluid density, fluid temperature, and fluid pressure.

Transit time for a signal to move a known distance between a transmitter and a receiver is determined for two separate sing-around circuits. Thereby, the transit-time shift velocity or sound velocity difference is determinable due to the fluid flow velocity. From the transit-time shift velocity, the flow velocity can be determined by understanding the trigonometric relationship between directional placement of each transmitter and receiver.

In the inventive circuit, an audio signal is generated from a transmitter and detected by a receiver. A portion of the audio signal reaches the receiver. The audio signal is converted into an electronic signal that is sent to a triggering system. The electronic signal may be boosted by an amplification circuit sufficient to create a triggering signal.

In the triggering system, the electronic signal may be amplified to assist in overcoming attenuation of the audio signal. Following optional amplification, the signal is rectified and gathered into a substantially half wave form. Spurious signals that are generated are filtered out by a gate or digital filter. The digital filter is tuned to anticipate approximately the time period when actual signals should pass therethrough and the digital filter simply eliminates any other signals that come outside the anticipated signal time window. Following digital filtration, the wave form is converted into a square wave and optionally changed in pulse width to optimize it as a triggering signal. The triggering signal is then ultimately sent to a pulser that instructs the transmitter to generate another audio signal.

A "keep-alive" circuit is also provided in the sing-around loop for the occasion where no signal is detected to be cycling within the loop. The keep-alive circuit is configured to look for a pulse coming from upstream in the circuit loop. It looks for a pulse of a particular waveform, namely the square wave, and of a particular pulse width that is characteristic of that which was made of the circuit following digital filtration and conversion into a square wave. Where the anticipated signal is not received within a particular time window, the "keep-alive" circuit generates its own signal, directed to the pulser, that instructs the transmitter to generate another audio signal in the direction of the receiver.

In any event, a pulse signal is generated and directed to the transmitter. At this point, a new audio signal is generated from the transmitter and detected by the receiver. After a number of cycles, the "sing-around" circuit settles down to its designed cycling time. The amount of time required to relay the signal from the receiver around to the transmitter is known. The largest time lapse in the circuit is the time required for the audio signal to bridge the distance between the transmitter and the receiver. As such, the speed of sound in the known multiple-component fluid can be extracted from the total cycling time of the circuit.

It is therefore an object of an embodiment of the present invention to provide a system that overcomes the problems of the prior art. It is also an object of an embodiment of the present invention to provide a system for the measurement of fluid flow in a conduit without constricting or redirecting the flow of the fluid.

It is also an object of an embodiment of the present invention to provide a sing-around circuit to measure flow of a fluid that filters all spurious signals.

It is also an object of an embodiment of the present invention to provide a system for measurement of flow of a fluid that is being used in a dynamic system. It is also an object of an embodiment of the present invention to provide a system for the measurement and control of fluid flow that is being conveyed in a conduit.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to a system for measuring the flow velocity without such prior art burdens as constricting the fluid flow, obstructing the fluid flow, diverting the fluid flow, and significantly disturbing the fluid flow. The inventive system uses a plurality of sing-around circuits that simplifies flow metering compared to methods of the prior art.

Figure 1:
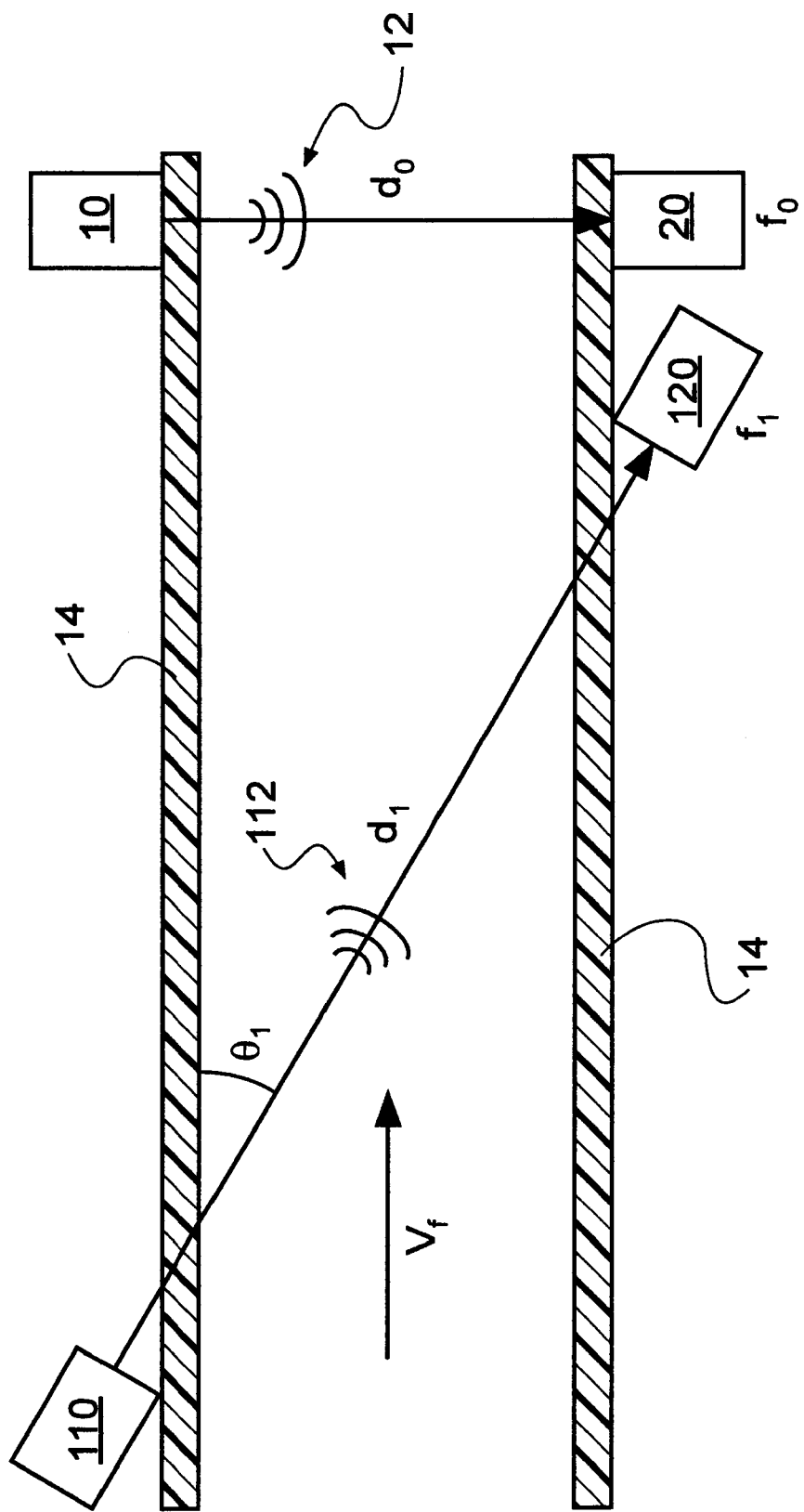
FIG. 1 is an elevational cross-section illustration of one embodiment of the present invention, wherein a pair of circuits evaluate both fluid composition and fluid flow velocity.

FIG. 1 shows the proposed transducer arrangement as well as the variables that determine the flow measurement. A substantially linear conduit 14 is seen in elevational cross section. Flow velocity, $V_f$, can be derived from equations that relate variables, temperature, and pressure to flow velocity. The flow velocity difference between two audio pulses is determined by measuring the transit-time shift that is experienced due to an audio signal being swept along the flow path, and converting this velocity difference to the flow rate in the conduit 14. The velocity is calculated by using two sing-around systems and converting the obtained frequency, f, into transit time.

There are four variables that affect the transit time of sound in a fluid. They are density, temperature, pressure, and velocity of the fluid. In order to cancel the effect of the first three variables, two sing-around circuits are used as depicted in FIG. 1. Transit time $t_0$, for a signal 12 to move distance $d_0$ between a transmitter 10 and a receiver 20 is affected by composition, temperature, and pressure only. Transit time $t_1$, for a signal 112 to span distance, $d_1$, between a transmitter 110 and a receiver 120 is affected by all four variables. By measuring the Doppler shift relative to transmitter 110 and receiver 120, the effects of composition, temperature, and pressure are effectively canceled. Thus, the sound velocity difference due to fluid flow velocity $V_\Delta$, is calculated as follows:

$$V_\Delta = V_1 - V_0 \quad \text{EQ 1.0}$$

The sounding velocity for each system is measured as follows:

$$V_0 = \frac{d_0}{t_0} \quad \text{EQ 2.0, 2.1}$$

$$V_1 = \frac{d_1}{t_1}$$

Subsituting these velocities into Equation 1.0 yields:

$$V_\Delta = \frac{d_0}{t_1} - \frac{d_0}{t_0} \quad \text{EQ. 3.0}$$

The output of the sing-around circuit is not transit time, but frequency, f. This requires the substitution of the following into Equation 3.0.

$$t = \frac{1}{f} \quad \text{EQ. 4.0}$$

This yields:

$$V_\Delta = d_1 f_1 - d_0 f_0 \quad \text{EQ. 5.0}$$

The results of Equation 5.0 must now be adjusted for the velocity component flowing parallel to the pipe.

Figure 2:
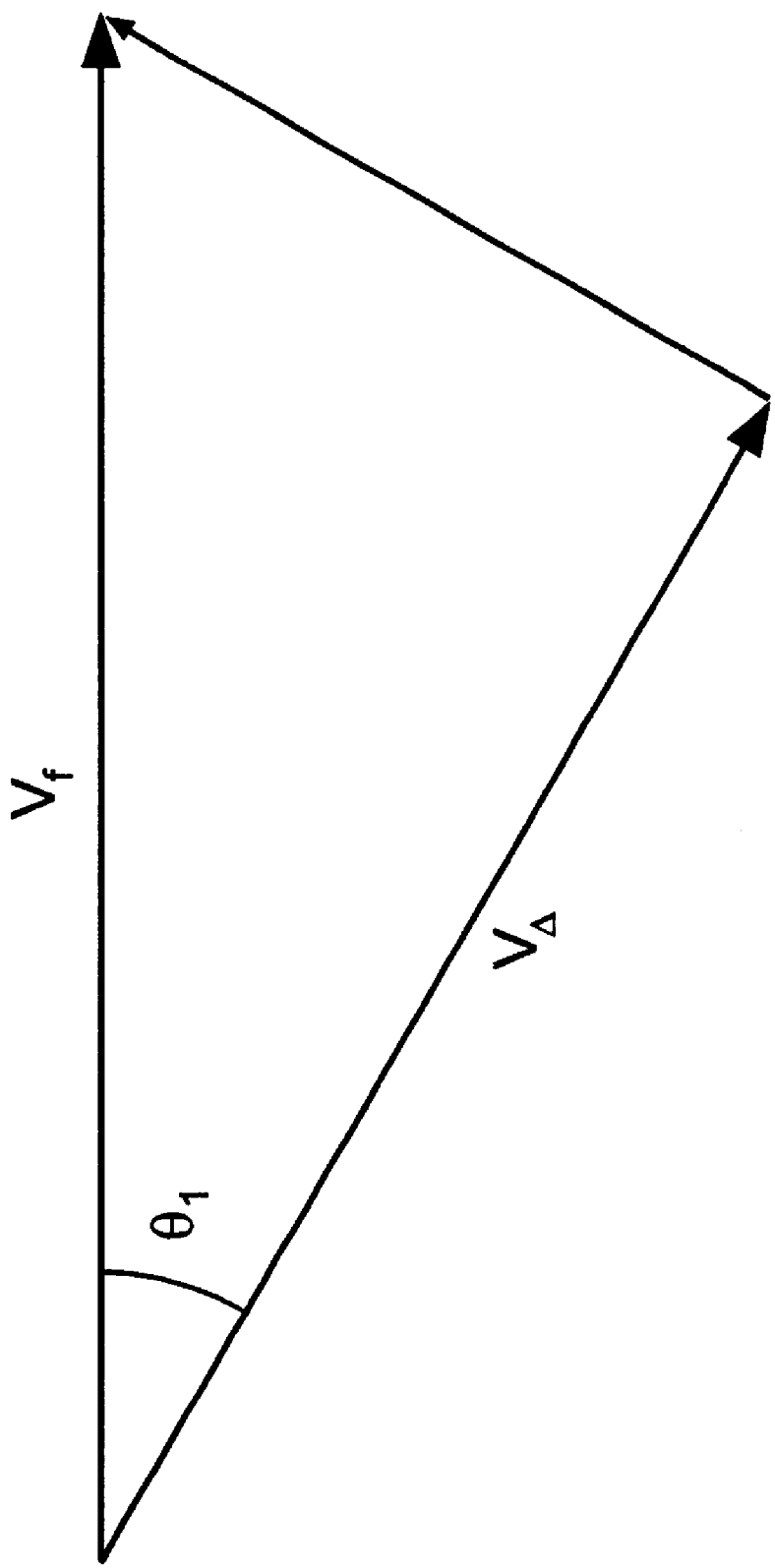
FIG. 2 is a depiction of the relationship of the parallel flow component that is derivable from use of the inventive system.

FIG. 2 illustrates this adjustment. Therein it can be seen that the relationship to the parallel flow component is given. This relationship is:

$$V_f = \frac{V_\Delta}{\cos(\Theta_1)} \quad \text{EQ. 6.0}$$

Equation 7 is obtained by substituting Equation 5.0 into Equation 6. Equation 7 is used to calculate flow velocity.

$$V_f = \frac{(d_1 f_1 - d_0 f_0)}{\cos(\Theta_1)} \quad \text{EQ. 7.0}$$

A distinct advantage exists in the inventive system where flow calculation is greatly simplified by the elimination of dependency upon the variables of density, temperature, and pressure. Thus, transmitter 10 and receiver 20 provide a baseline, known audio-signal speed and pressure. Thus, transmitter 10 and receiver 20 provide a baseline, known audio-signal speed in the fluid composition. Transmitter 110 and receiver 120 along with the reception of oblique-angle audio signal 112, earlier than if no flow were present, allows for the determination of flow velocity within conduit 14. Preferably, angle Θ may be 45° or less. As angle Θ becomes smaller and approaches 0°, the accuracy of measuring linear flow may increase.

The combination of transmitter 10 and receiver 20 in connection with transmitter 110 and receiver 120 allow for a dynamic control capability for a system wherein the density and mass flow of the fluid must be constantly reevaluated and adjustments made therefor in order to achieve optimum system operation. As an example thereof, a natural gas-fired system such as a gas burner for a boiler, a low $NO_x$ burner, a rotary kiln, a gas combustion turbine, or other systems is supplied with natural gas and the inventive system depicted in FIG. 1. The inventive system would comprise conduit 14 and transmitters 10,110 and receivers 20,120 positioned before the gas combustion apparatus.

Figure 3A:
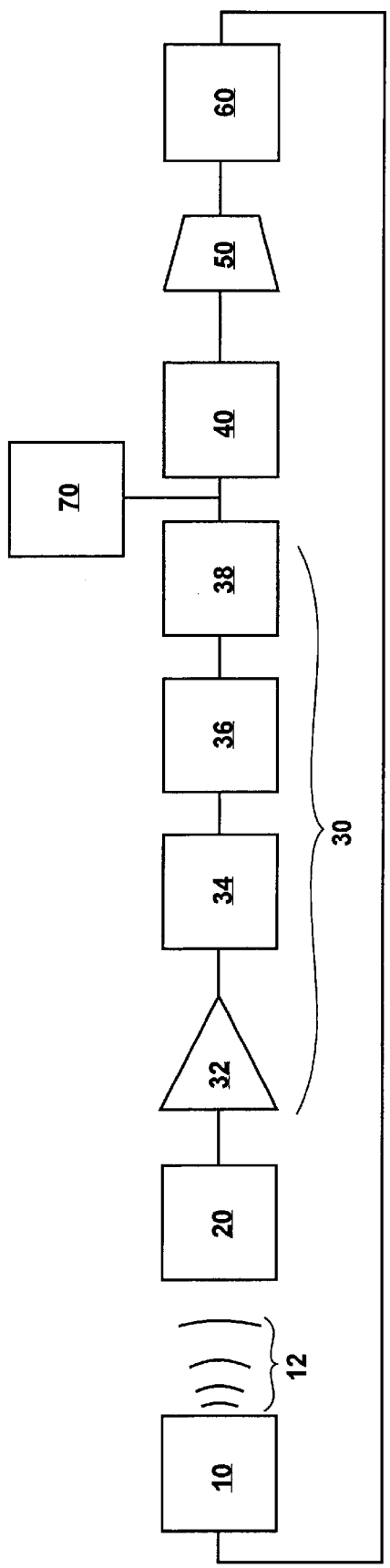
FIG. 3a is a block diagram of a sing-around circuit that is part of the inventive system.
Figure 3B:
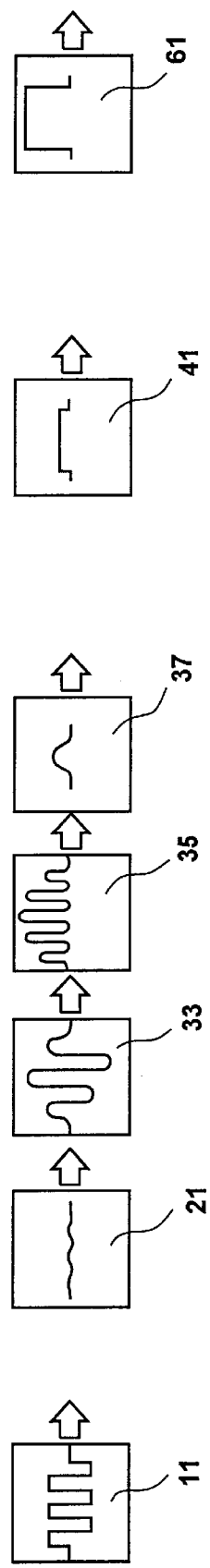
FIG. 3b is an illustration of the inventive signal processing that corresponds to the sing-around circuit of the present invention.

FIG. 3a is a block diagram illustration of the circuitry portion inventive system. FIG. 3b further illustrates the circuitry portion signal that is being manipulated. The block diagrams in FIG. 3b that are positioned immediately beneath their corresponding block diagrams in FIG. 3a, and illustrate the signal as processed in the respective block diagrams of FIG. 3a.

An example of the circuit in operation is given below. Transmitter 10 generates an audio signal 12 that is broadcast in the direction of receiver 20. Audio signal 12 moves through a medium between transmitter 10 and receiver 20. Typically, the medium is a solid, a liquid, a gas, or any combinations thereof. Receiver 20 detects audio signal 12 and an electronic signal 21 is generated within receiver 20 as illustrated in FIG. 3b.

The remainder of the inventive circuit is a means for determining the signal delay between the transmitter and the receiver. The inventive circuit includes a high frequency signal as defined below, propagating through a fluid medium, and the configuration of a trigger circuit 30.

The signal is transmitted to an amplifier 32 in order to overcome the likely extreme attenuation of the broadcast signal that occurs between transmitter 10 and receiver 20.

The amplified signal 33 is then transmitted to a rectifier 34 to substantially eliminate the sinusoidal nature thereof. A rectified signal 35 is then transmitted to an envelope detection circuit 36 that converts rectified signal 35 into a half wave 37. Half wave 37 is then transmitted to a masking or gate circuit. The masking or gate circuit acts as a digital filter. The inventive circuit is configured to expect reception of half wave 37 at digital filter 38 within a certain time window. All spurious signals that arrive at digital filter 38 outside the time window, are substantially eliminated thereby. Following the digital filtration of half wave 37, the signal is transmitted to a pulse width adjuster 40. Pulse width adjuster 40 is placed within the inventive system to provide an adequate triggering signal to cause transmitter 10 to repeat its transmission to receiver 20. Typically, the pulse width of half wave 37 will be inadequate, namely too narrow, to facilitate the triggering of a new pulse from transmitter 10. Therefore, a TTL or square wave 41 is generated at pulse width adjuster 40.

The inventive circuit also uses a "keep-alive" circuit 50 that is configured to send a square wave approximately equivalent to square wave 41 to a pulser 60. Pulser 60 receives either square wave 41 from pulse width adjuster 40 or a similar square wave from keep alive circuit 50. Pulser 60 then in turn generates a signal 61 that induces transmitter 10 to repeat the cycle.

A digital readout 70 is placed somewhere after digital filter 38 in order to provide an observer with information regarding the cycling time of the inventive system. Digital readout 70 may be configured to display a frequency of the total cycling time of the inventive system. The total cycling time of the inventive system is correlatable to different fluid compositions and the respective speeds of sound therein. Digital readout 70 may display a cycling time frequency that, depending upon the medium being tested, will allow the observer to compare the frequency to known binary fluid systems and to arrive at an estimated composition ratio of the components thereof. Alternatively, digital readout 70 may simply relay its information to another system that assists to correlate the fluid's audio transmission characteristics to its composition ratio.

After employment of the means for determining the signal delay between the transmitter and the receiver, a means for determining a settled sing-around frequency is employed for a known fluid. An example thereof is pumping ordinary water through conduit 14 and determining the portion of the settled sing-around frequency that is indigenous to the water transport of the signal and the portion of the settled sing-around frequency that is indigenous to the circuitry. As illustrated in FIG. 1, a means for determining the settled sing-around frequency may be used for transmitter 10 and receiver 20 and separately for transmitter 110 and receiver 120.

A means for correlating the signal delay to a database is employed for the fluid. In its simplest form, the means for correlating the signal delay to a database includes the decision whether to eliminate the signal processing time between receiver 20 and transmitter 10 from the total cycling time of the inventive circuit or whether to ignore it. Another portion of the means for determining the signal delay between the transmitter and the receiver includes empirical data and digital readout 70.

In a specific embodiment of the present invention, transmitter 10 and receiver 20 are separated by a distance of less than about 10 cm. In this embodiment of the present invention, transmitter 10 and receiver 20 may be spaced apart in a range from about 0.5 cm to about 100 cm and the exposed surface area of each is in a range from about 1 cm$^2$ to about 20 cm$^2$. The surface area of each exposed portion thereof is preferably less than about 10 cm$^2$.

The inventive system uses a duplicate pair of circuits from which the flow velocity of the fluid can be determined. It can be seen that transmitter 10 and receiver 20 are configured to transmit audio signal 12 substantially perpendicular to the direction of flow $V_f$ of a multiple-component fluid within a conduit 14. A second system is configured to transmit an oblique-angle audio signal 112 at an angle $\Theta$, between a transmitter 110 and a receiver 120. Transmitter 10 and receiver 20 are used in conjunction with transmitter 110 and receiver 120 in order to assist to determine the flow velocity, $V_f$ of the fluid within conduit 14.

The speed of audio signal 12 as it passes through the fluid is determined between transmitter 10 and receiver 20 as set forth above. Because the fluid composition may be presumed to be substantially homogeneous within conduit 14 between transmitter 10 and receiver 20 and between transmitter 110 and receiver 120, and because the distances d0 and d1 are known, the angled configuration of transmitter 110 and receiver 120 in relation to the direction of flow will cause oblique-angle audio signal 112 to reach receiver 120 earlier than anticipated by a factor of approximately the linear flow rate multiplied by the trigonometric cosine of the angle $\Theta$. In the past, calculation of flow by similar methods required dependency upon such variables as system pressure, system temperature, and the composition, i.e. density, of the fluid. With the inventive method, system pressure, system temperature, and system composition are substantially eliminated as data from the duplicate pair of circuits is compared.

The following tests were conducted using the double sing-around circuit system of the present invention to calculate the flow rate of a known multiple-component fluid, namely He/N. Test 1 was conducted with air at about 73.2° F. Air was passed through conduit 14 at a known rate of 20 cuft/hr. Separation between transmitter 10 and receiver 20, do was about 1.695 inches. The inventive system settled down to a cycling frequency of about 7.833 kHz from which it was determined that oblique-angle audio signal 112 was carried forward to receiver 120 at a rate of about 0.0135 inches per microsecond. By use of a simple trigonometric calculation, the flow rate was found to be about 20 ft$^3$/hr.

Tests 2 through 13 were also conducted using helium and nitrogen. The gas flow rate was derived from the data in a manner similar to that for the gas flow rate of Test 1.

| Test No. | Gas | Thermocouple Reading (deg. F.) | Frequency (kHz) | Gas Flow Rate (CFH) |
|---|---|---|---|---|
| | | Run 1 | | |
| 2 | 45% He/55% N | 73 | 10.321 | 20 |
| 3 | 35% He/65% N | 73 | 9.628 | 20 |
| 4 | 25% He/75% N | 73 | 9.062 | 20 |
| 5 | 15% He/85% N | 74 | 8.565 | 20 |
| 6 | 5% He/95% N | 74 | 8.131 | 20 |
| | | Run 2 | | |
| 7 | 45% He/55% N | 73 | 10.331 | 20 |
| 8 | 35% He/65% N | 73 | 9.629 | 20 |
| 9 | 25% He/75% N | 73 | 9.058 | 20 |
| 10 | 15% He/85% N | 73 | 8.561 | 20 |
| 11 | 5% He/95% N | 73 | 8.128 | 20 |
| | | Run 3 | | |
| 12 | 45% He/55% N | 73.2 | 10.333 | 20 |
| 13 | 45% He/55% N | 73.5 | 10.335 to 10.341 | 140 |

Test 13 was carried out at a substantially higher flow rate. The cross-sectional shape of conduit 14 was a circular pipe.

Because the components of the multiple-component fluid may be known, and because correlations may be on hand that describe the multiple-component fluids and their quantitative component ratios, the overall flow velocity of the gas and a "snap shot" of its quality may be determined with the inventive system in order to optimize the device that uses natural gas combustion. Additionally, where combustion product effluents must be monitored for environmental reasons, gas quality such as a high sulfur content may allow a combustion system to be adjusted in order to minimize the release of undesirable pollutants to the atmosphere.

Distinct advantages exist with the present invention. Evaluation of a fluid by the inventive method and system is essentially non-intrusive into a container such as conduit 14. Additionally, the sing-around circuitry for use in a gaseous system with an audio signal in the megahertz range allows for error band detection. At a high frequency, the error band does not change substantially if at all such that the inventive system may be used by broadcasting a range of frequencies at different times and any errors or time delays will remain consistent.

The present invention is particularly well suited for the determination of fluid density, fluid proportions of known components, flow velocity, and mass flow rate. Because distances between transmitters and receivers are known, fluid densities may be approximated from fairly known systems. For example, with a liquid, the flow velocity of sound in a fluid is proportional to the square root of the bulk modulus of elasticity of the liquid uncompressed, divided by the density of the fluid. For a gas that may be assumed to be ideal, the velocity of sound is proportional to the square root of the product of the heat capacity ratio, the universal gas constant, and the temperature. Thus, where a system is fairly well known, such as irrigation water, a slurry, or a multiple-component natural gas feed, the density of the fluid may be estimated from data for known pure components.

One example of the usefulness of the inventive system is the estimation of the percent solids of the slurry being delivered through a conduit such as a ball mill effluent for a copper flotation product stream in the mining industry. By assuming that the slurry is substantially uniformly mixed, signal 12 as it propagates through conduit 14 will reach receiver 20 faster with copper in a slurry because the speed of sound through copper is higher than through water.

Another application of the inventive system is the determination of turbidity in irrigation water. Where the velocity of sound through substantially pure water is known or may be calibrated for a given system, an arrived-at $V_f$ of a velocity higher than $V_f$ for water may provide an estimation of the amount of silt or other material that is being carried in the irrigation water.

Another application of the present invention is the determination of pollutants in effluent water as it exits a processing plant and as it is evaluated for release to the surroundings or for further processing. Another application of the present invention is the evaluation of mill pond recycle water for the evaluation of unexpended reactants, for example, the alkaline content in mill pond water for a gold cyanide operation.

Another application of the present invention is a marine speedometer. Instead of measuring the flow of a fluid through a conduit, the configuration of transmitters 10, 110 and receivers 20, 120, as depicted in FIG. 1 may be affixed to the hull of a watercraft or otherwise. Thereby the flow velocity of the water may be determined.

For each of these discussed applications of the present invention and for others, regular comparison of the estimation with a traditional analysis such as a Marcy® cup for a slurry, or wet chemical analysis for unexpended reactants, is recommended, as natural systems may change seasonally and regionally.

Example 14 is a paper example of the present invention applied to a copper flotation cell concentrate as it overflows into a trough and channels into a conduit. Conduit 14 has an inner diameter of 0.25 meters. The system is calibrated for mill water by comparing it to a known velocity of sound in pure water of about 1,450 meters/sec. The slurry is then diverted into conduit 14 and a second measurement is taken. The velocity of audio pulse 12 is measured at about 2,000 meters/sec. By using a known velocity of sound in copper at 3560 meters/sec, it is estimated by trial and error correlation that the slurry contains about 26% copper solids. A later sample is taken and the velocity of audio pulse 12 is measured at about 2,200 meters/sec. From this data, it is estimated by trial and error correlation that the slurry contains about 35.5% copper solids. Such percent solids readings may be compared for example with a Marcy® cup measurement to further correlate the audio pulse data to copper flotation slurries and thereby determine slurry densities.

Continuing with Example 14, the inventive system is used, including transmitters 10 and 110 and receivers 20 and 120 in connection with a determination of a flow velocity of the copper slurry in conduit 14. The flow velocity is determined to be about 0.5 meters/sec. From that flow velocity, and using the 35.5% copper solids estimation, a mass flow rate of about 280 kg of copper per hour is calculated.

It may now be understood that estimating a fluid density may be combined by the inventive system, with a method of calculating a fluid flow velocity in order to arrive at mass flow evaluations. The inventive system is particularly useful for dynamic, multiple-component systems where, although the components may be known to the system, the relative proportions of the components may change in response to system load changes caused by external disturbances and the like.

The percent solids correlations may then be used to calculate fluid densities and also to calculate fluid mass flow rates. By the same token, the humidity of air may be estimated by comparing known velocities with measured velocities and correlating the measured velocity with moisture in the air.

Example 15 is a paper example of measuring flow velocity of a gas stream past a flat plate. The flat plate is affixed to an aircraft and measurements of flow velocity are taken during a flight. It is assumed that the air stream through which signal 12 and signal 112 pass, is fully developed and boundary layer effects are negligible. Transmitter 10 and receiver 20 are separated by about 3 cm. Transmitter 110 and receiver 120 are separated by about 5 cm. Transmitter 10 and receiver 20 are configured in a substantial vertical arrangement in relation to the flow of air past the flat plate. Transmitter 110 and receiver 120 are configured at an angle that subtends from the horizontal by about 30°.

Capacitive coupling effects occur due to both the magnitude of the capacitive charge and the surface areas of transmitters 10, 110 and receivers 20, 120 that are exposed. Transmitters 10, 110 generate a signal in a frequency range between about 100 kHz to about 10 MHz. In this application, where audio signals 12, 112 are transmitted through a gas, attenuation thereof is extreme due to high frequencies. A frequency for a gaseous system is in a range from about 500 KHz to about 5 MHz, preferably about 1 MHz. At this frequency range, attenuation may exceed 50%, may exceed 90%, and may exceed 99.9%.

In order to avoid sending a spurious signal generated by capacitive coupling substantially simultaneously with audio signals 12, 112, audio signals are generated in a pulse width in a range of about 0.1 microseconds to about 5 microseconds. Preferably, the pulse width is in a range from about 1 microsecond to about 3 microseconds, and more preferably about 2 microseconds. Due to the extreme narrowness of the pulse width of audio signals 12, 112, and due to the extreme attenuation of such a high frequency signal in a gaseous medium, reception thereof by receivers 20, 120 is problematic. As such, received signal 21 is amplified in amplifier 32 for a gain between about 100 and about 10,000, preferably 200 and 5,000, and most preferably about 1,000. A variable-gain amplifier may be used to tune the inventive system such that received signal 21 is amplified sufficiently to be further processible. In the gaseous system, the size of the gain in amplifier 32 is generally configured to be directly proportional to the frequency of the audio signal. In this embodiment, the gain is about 1,000, the frequency is about 1 MHz, and the pulse width is about 2 microseconds.

Following the conversion of received signal 21 into amplified signal 33, amplified signal 33 is converted into rectified signal 35. Thereafter, rectified signal 35 is manipulated into a half wave form, into a half wave 37, and directed further. Half wave 37, whether a spurious signal or a desired signal, is directed though digital filter 38.

As previously explained, a time window during which the desired signal is received is closed to all other signals such as a signal generated due to capacitive coupling between transmitters 10, 110 and receivers 20, 120. Typically, because the pulse width is about 2 microseconds wide, pulse width adjuster 40 is provided to make half wave 37 into square wave 41. Pulse width adjuster 40 is capable of both diminishing the size of half wave 37 or increasing the its size. Typically, the pulse width is about 2 microseconds and pulse width adjuster 40 adjusts the size of half wave 37 to be approximately 10 microseconds wide. The advantage to making the pulse width approximately 10 microseconds wide is that the circuit does not accidentally trigger more than once within a preferred time period.

Square wave 41 passes further through the circuit to keep-alive circuit 50. Keep-alive circuit 50 waits for a preferred time period to receive a detected signal and if no signal is received, keep-alive circuit 50 generates its own signal to pulser 60 in order to repeat generation of audio signal 12. In this embodiment, the timing window, or waiting time, is between about 0.1 and 20 milliseconds, preferably about 20 and about 15 milliseconds, and most preferably about 10 milliseconds.

Square wave 41 or a square wave from keep-alive circuit 50 is generated. In any event, a square wave of about 10 microseconds width enters pulser 60 and is of sufficient voltage, amplitude and duration to cause transmitters 10, 110 to repeat the transmission of audio signals 12, 112.

The time delay between the transmission of audio signals 12, 112 and the reception thereof at respective receivers 20, 120 is significantly larger than all other elapsed time within the circuitry of the inventive system. As such, the elapsed time to process received signal 21 as a part of the entire cycling time of the inventive system may either be disregarded or subtracted. Subtraction of the signal processing time as part of the total elapsed time of each cycle becomes less important as the distance between transmitters 10, 110 and receivers 20, 120 increases. Each pulser 60 generates a TTL square wave voltage spike in a range from about 60 volts to about 220 volts, preferably about 120 volts. In response, transmitters 10, 110 generate respective signals that propagate to receivers 20, 120.

Each pulser 60 is designed to repeat pulses at a rate between about 0.1 to about 100 KHz, preferably between about 2 to about 10 KHz. In other words, elapsed time for one cycle between a first pulse and a second pulse is in this kilohertz range. The rate is dependent upon the speed of the audio signal as it propagates through the medium being tested and the distance between transmitters 10, 110 and receivers 20, 120.

A $V_A$ of 100 miles per hour is determined between the two circuits and, based upon the angle, θ, Vf is calculated to be about 115 miles per hour.

Figure 4:
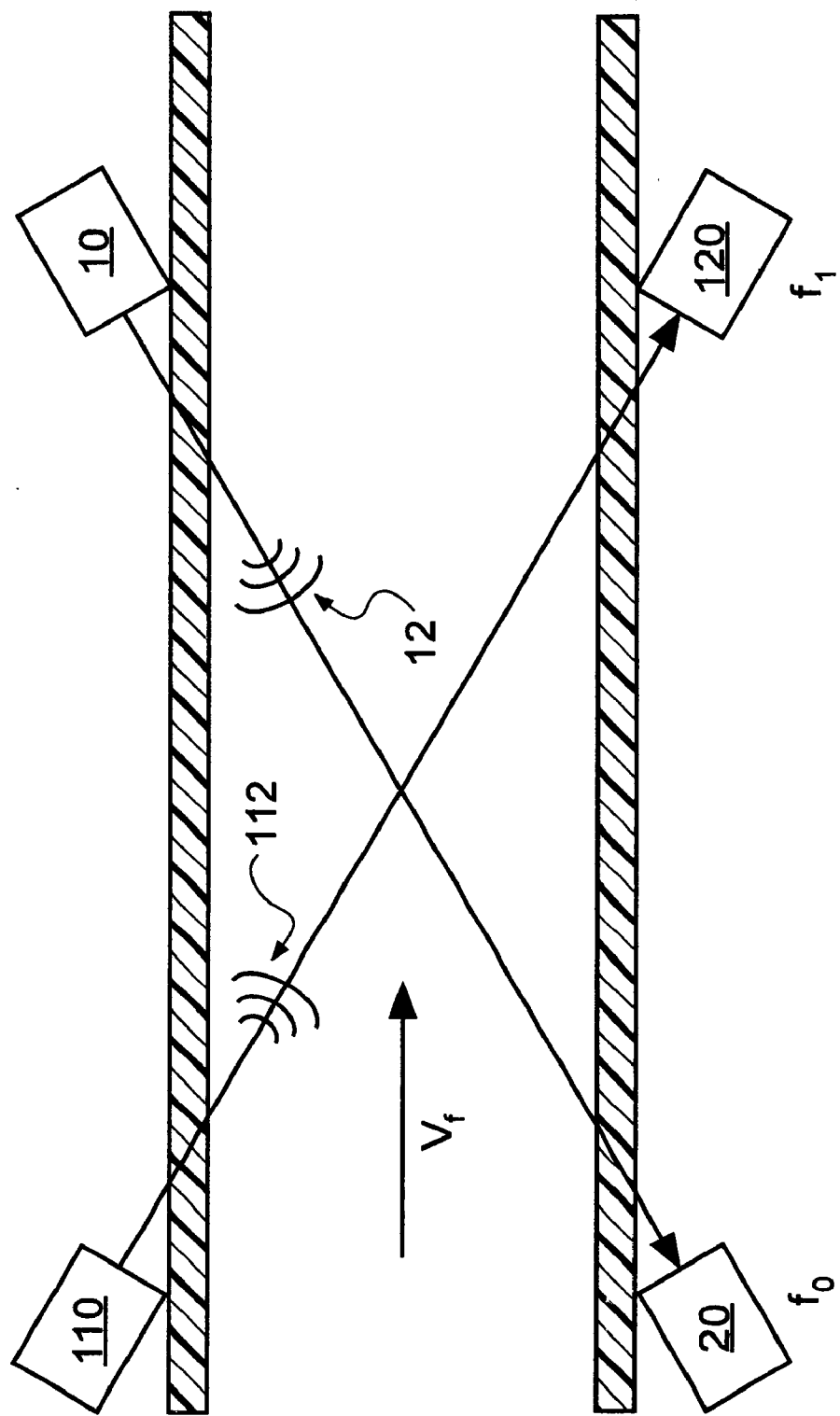
FIG. 4 is an alternative embodiment of the present invention, where a first signal is directed downstream and a second signal is directed upstream.

FIG. 4 is an embodiment of the present invention, wherein two sing-around circuits are used with respective transmitters 10, 110 and receivers 20, 120 that are configured to send audio signals 12, 112 at oblique angles through the fluid medium within conduit 14. The advantage of configuring both transmitters and receivers at oblique angles makes the measurement more accurate than with using a perpendicularly configured audio signal circuit.

Figure 5:
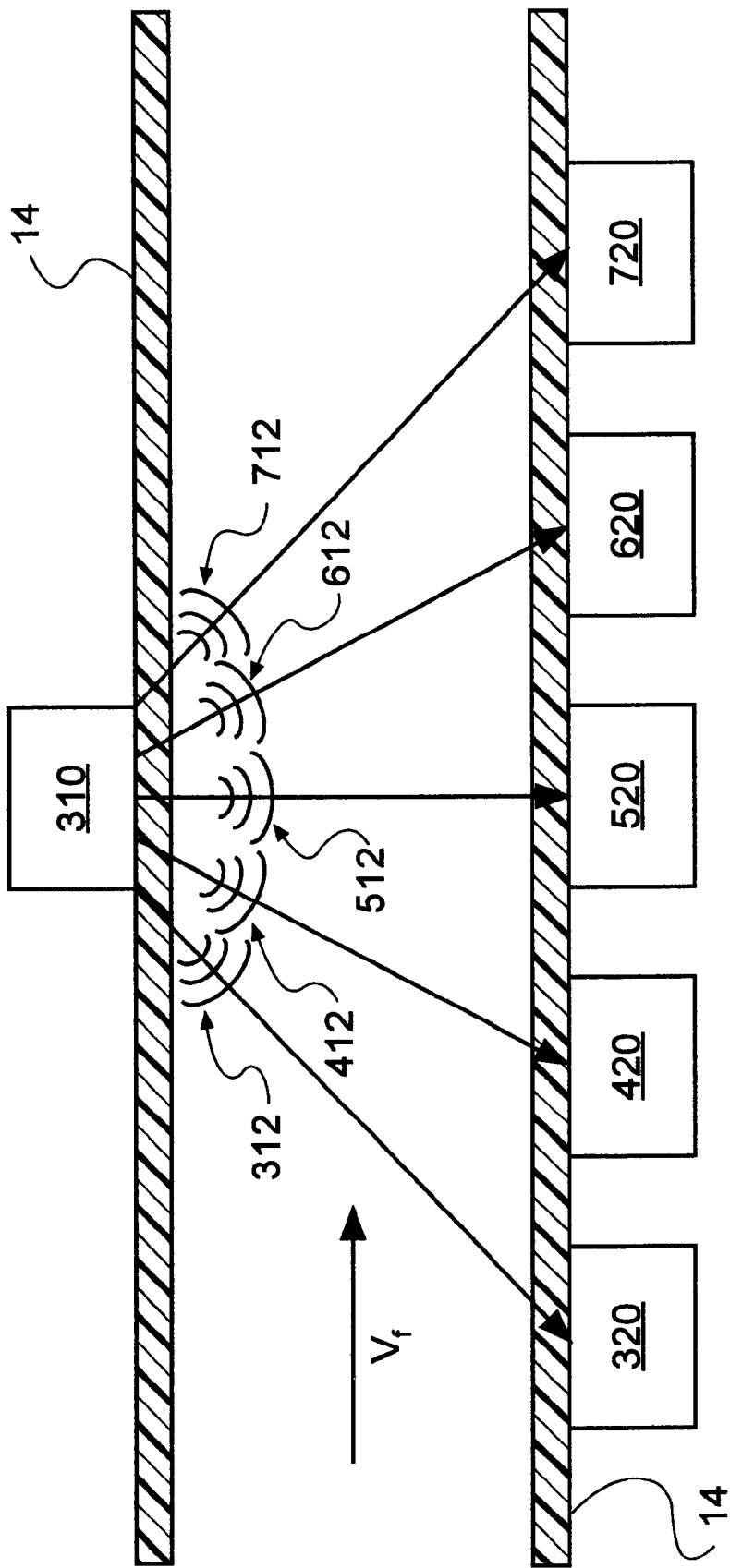
FIG. 5 is an alternative embodiment of the device depicted in FIG. 2, wherein an integral transmitter generates a signal that can be detected by more than one receiver.

In another embodiment depicted in FIG. 5, a transmitter 310 sends multiple signals 312, 412, 512, 612, and 712 to multiple receivers 320, 420, 520, 620, and 720, respectively. This inventive configuration allows for an average flow velocity to be found by using the $V_A$ that is found between permutations of transducer pairs. A distinct advantage may be appreciated by the embodiment of the present invention illustrated in FIG. 5. With a plurality of receivers, an average flow velocity may be calculated during unstable conditions.

Figure 6:
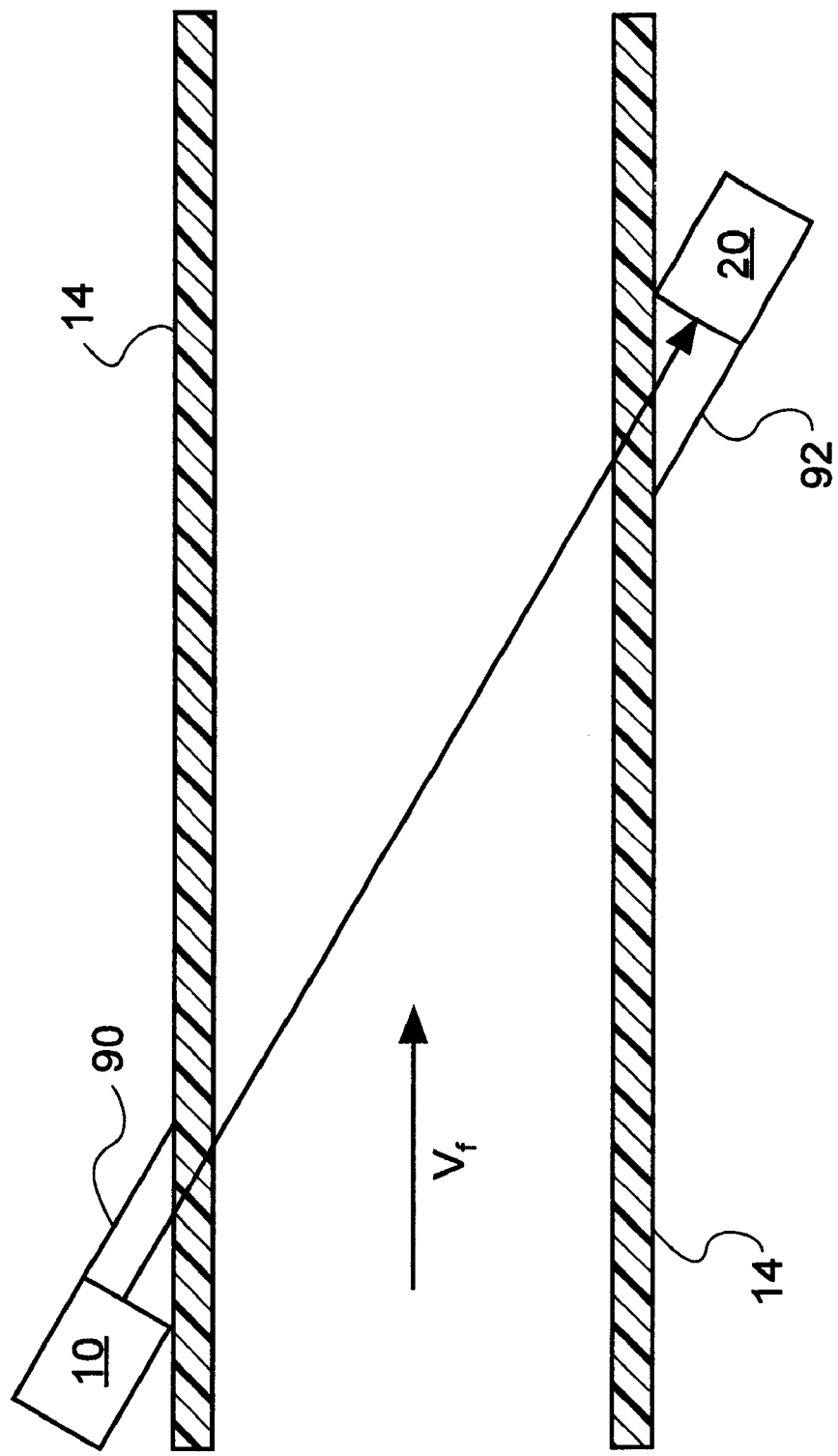
FIG. 6 is an embodiment of the present invention, wherein transducers are mounted on the surface of the conduit and the audio signal is transmitted through the conduit wall.

FIG. 6 illustrates an alternative embodiment of the present invention, wherein it can be seen that transmitter 10 and receiver 20 are mounted on the surface of conduit 14 such that no protrusion or depression is made into conduit 14. A transmitter fitting 90 and a receiver fitting 92 are seen as being substantially mounted onto the surface of conduit 14 between respective transmitter 10 and receiver 20. With this embodiment, the velocity of sound through transmitter fitting 90, receiver fitting 92, as well as through the material of conduit 14 should be known so as to adjust the calculation.

Figure 7:
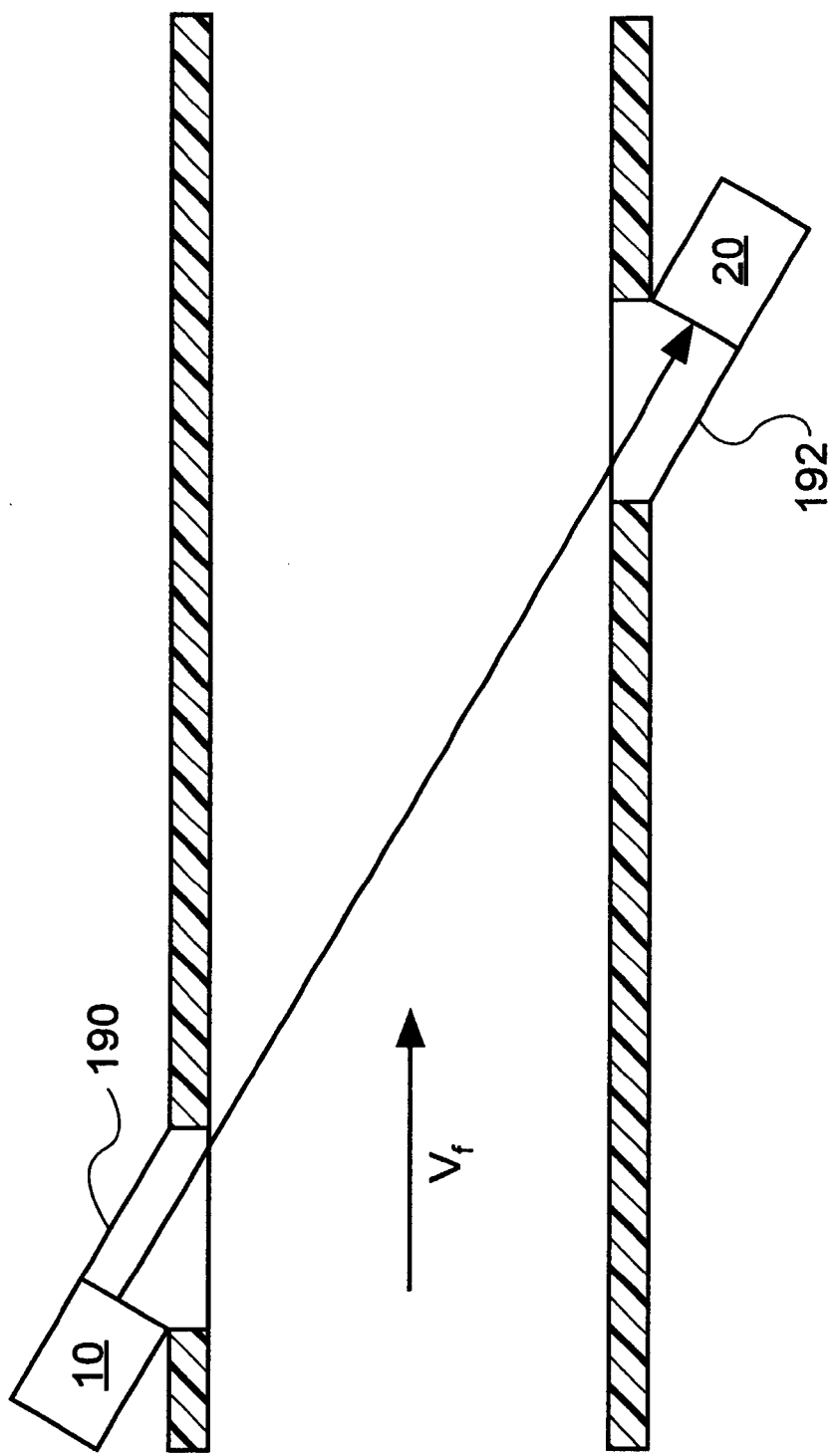
FIG. 7 is an alternative embodiment of the present invention, wherein the transmitter and receiver are fitted into the conduit wall such that the audio signal is transmitted through an optimized material.

FIG. 7 is an alternative embodiment of the present invention, wherein it can be seen that the audio signal is not transmitted through the wall of conduit, rather it is transmitted through an optimized material to make an invasive transmitter fitting 190 and an invasive receiver fitting 192 that may also make up transmitter fitting 90 and receiver fitting 92 and through the fluid at large.

Figure 8:
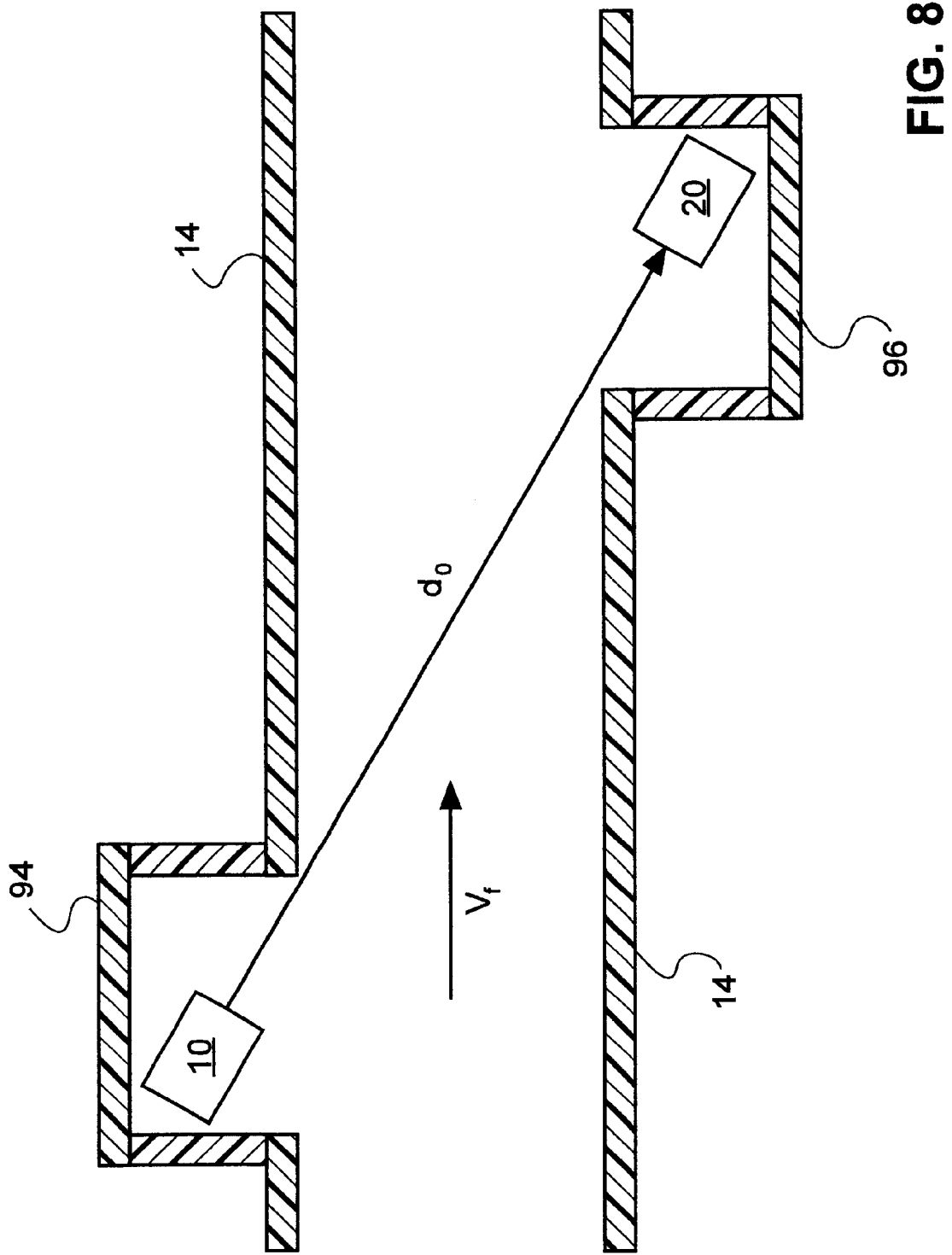
FIG. 8 is an alternative embodiment of the present invention, wherein the transducers are located inside the conduit, but not directly in the flow path.

FIG. 8 is an alternative embodiment of the present invention, wherein it can be seen that the transducers are located inside conduit 14 in specially constructed section 94, 96 of conduit 14 such that transducers are located inside conduit 14 but are not directly in the flow path.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

We claim:

1. A method for determining the flow velocity of a fluid comprising:

providing a fluid that flows in a given direction;

transmitting and receiving a first pulse perpendicular to said given direction across a first known distance within said fluid;

transmitting and receiving a second pulse at an oblique angle to said given direction, across a second known distance within said fluid;

determining respective velocities for said first and second pulses;

calculating the difference between said respective velocities;

using said difference to determine said flow velocity; and comparing said flow velocity to a set-point flow velocity.

2. A method for determining the flow velocity of a fluid according to claim 1, wherein determining respective velocities for said first and second pulses comprises using a first sing-around circuit for said first pulse and a second sing-around circuit for said second pulse.

3. A method for determining the flow velocity of a fluid according to claim 1, wherein transmitting and receiving a second pulse is directed with an upstream directional component.

4. A method for determining the flow velocity of a fluid according to claim 1, wherein transmitting and receiving a second pulse is directed with a downstream directional component.

5. A method for determining the flow velocity of a fluid according to claim 1, wherein said fluid that flows is within a conduit.

6. A method for determining the flow velocity of a fluid according to claim 1, wherein transmitting and receiving comprises affixing a plurality of transmitters and respective receivers on said conduit.

7. A method for determining the flow velocity of a fluid according to claim 1, wherein transmitting and receiving comprises affixing a single transmitter and a plurality of receivers on said conduit.

8. A method of controlling a fluid flow system comprising:
providing a substantially linear conduit section having boundaries and a flowing fluid therein;
transmitting a first pulse perpendicular to said substantially linear conduit section between said boundaries across a first distance;
transmitting a second pulse at an oblique angle to said substantially linear conduit section between said boundaries across a second distance;
determining respective velocities for said first and second pulses through said fluid;
calculating the difference between said respective velocities;
using said difference to obtain a flow velocity;
comparing said flow velocity to a set-point flow velocity; and
optionally adjusting said flow velocity.

9. A method of controlling a fluid flow system according to claim 8, wherein transmitting comprises affixing a plurality of audio signal transmitters to said conduit and affixing a plurality of audio signal receivers to said conduit.

10. A method of controlling a fluid flow system according to claim 8, wherein said fluid flow system includes irrigation water.

11. A method of controlling a fluid flow system according to claim 8, wherein said fluid flow system includes a slurry.

12. A method of controlling a fluid flow system according to claim 8, wherein said fluid flow system includes a gas.

13. A method of controlling a fluid flow system according to claim 8, wherein said fluid flow system includes a combustion gas.

14. A method of controlling a fluid flow system according to claim 8, wherein said fluid flow system includes a plurality of sing-around circuits.

15. A system for measuring flow velocity of a fluid comprising:
a plurality of sing-around circuits, each said sing-around circuit including an acoustic transmitter, a receiver and
a means for determining a settled sing-around frequency for each sing-around circuit, wherein said means for determining a settled sing-around frequency for each sing-around circuit comprises:
an amplifier in communication with said receiver;
a rectifier in communication with said amplifier; and
a gate circuit in communication with said rectifier; and
a means for calculating transit-time shift between at least two of said plurality of sing-around circuits, said means for calculating transit-time shift employing each said settled sing-around frequency.

16. A system for measuring flow of a fluid according to claim 15, further comprising a flowing fluid contained in a conduit.

17. A system for measuring flow of a fluid according to claim 16, wherein said flowing fluid contains water.

18. A system for measuring flow of a fluid according to claim 16, wherein said flowing fluid contains a slurry.

19. A system for measuring flow of a fluid according to claim 16, wherein said flowing fluid contains a gas.

20. A system for measuring flow of a fluid according to claim 16, further comprising an apparatus that employs said flowing fluid.

21. A system for measuring flow of a fluid according to claim 15, wherein said acoustic transmitter is ultrasonic.

22. A method of determining the percent solids of a slurry comprising:
providing a slurry in a conduit;
generating a pulse through said conduit across a known distance;
calculating the velocity of said pulse across said known distance; and
correlating said velocity to the percent solids in said slurry.

23. A method of determining the percent solids of a fluid according to claim 22, wherein correlating said velocity to the percent solids in said fluid comprises estimating the speed of sound for the fluid portion of said slurry.

24. A method of determining the percent solids of a fluid according to claim 22, wherein said pulse is generated by a sing-around circuit.

25. A method of determining the percent solids of a fluid according to claim 22, further comprising determining the flow velocity of said slurry.

26. A system for measuring the flow of a fluid comprising:
a first transmitter and a first receiver, said first transmitter and said first receiver being separated by a first distance;
a second transmitter and a second receiver, said second transmitter and said second receiver being separated by a second distance;
each of said first transmitter and receiver and said second transmitter and receiver comprising:
a trigger circuit including a signal rectifier;
means for determining the signal delay between said transmitter and said receiver, wherein said means for determining the signal delay between said transmitter and said receiver has an alternative digital signal filter connected to said trigger circuit; and
means for calculating the transit-time shift caused by the flow of said fluid.

27. A system for measuring the flow of a fluid according to claim 26, further comprising means for eliminating an errant signal generated by capacitive coupling between said transmitter and said receiver.

28. A system for measuring the flow of a fluid according to claim 26, wherein said trigger circuit further comprises:

a signal amplifier connected to said receiver;

said signal rectifier connected to said signal amplifier;

a signal converter connected to said signal rectifier; and an alternative signal width adjuster connected to said signal converter.

29. A system for measuring the flow of a fluid according to claim 26, wherein said transmitter generates an audio signal in a frequency range from about 100 kHz to about 10 MHz.

30. A system for measuring the flow of a fluid according to claim 26, wherein said transmitter generates an audio signal with a frequency of about 1 MHz.

31. A system for measuring the flow of a fluid according to claim 26, wherein said transmitter generates a pulse with an initial pulse width in a range from about 0.1 microseconds to about 5 microseconds.

32. A system for measuring the flow of a fluid according to claim 26, wherein said trigger circuit has a signal amplifier with a gain between about 100 and about 10,000.

33. A system for measuring the flow of a fluid according to claim 26, wherein said square wave trigger circuit generates a square wave signal with a width of about 10 microseconds.

34. A system for measuring the flow of a fluid according to claim 26, further comprising a keep-alive circuit disposed between said receiver and said transmitter, said keep-alive circuit having a timing window in a range from about 0.1 to about 20 milliseconds.

35. A system for measuring the flow of a fluid according to claim 26, wherein said second pulse has a potential in a range from about 60 volts to about 220 volts.

36. A system for measuring the flow of a fluid according to claim 26, wherein elapsed time for one cycling of said system is measurable in a range from about 0.1 kHz to about 100 kHz.

37. A system for measuring the flow of a fluid according to claim 26, wherein said trigger circuit further comprises:

a signal amplifier connected to said receiver;

a signal rectified connected to said signal amplifier;

a signal converter connected to said signal rectifier; and a alternative signal width adjuster connected to said signal converter, wherein said transmitter generates an audio signal in a frequency range from about 100 kHz to about 10 MHz, wherein said transmitter generates an audio signal with an attenuation between said transmitter and said receiver in excess of about 50%, wherein said transmitter generates a pulse with an initial pulse width in a range from about 0.1 microseconds to about 5 microseconds, wherein said signal amplifier has a gain between about 100 and about 10,000, wherein said trigger circuit generates a square wave signal with a width of about 10 microseconds, wherein said pulse has a potential in a range from about 60 volts to about 220 volts, and wherein elapsed time for one cycling of said system is measurable in a range from about 0.1 kHz to about 100 kHz.

38. A method of controlling a dynamic fluid-supply system comprising:

providing a first transmitter and a first receiver separated by first fixed distance and with a fluid therebetween;

transmitting a first pulse from said first transmitter;

receiving said first pulse across said first fixed distance to create a first receiver signal;

creating a first trigger signal;

using said first trigger signal to transmit a repeat pulse from said first transmitter;

determining the signal delay between said first transmitting and first receiving;

providing a second transmitter and a second receiver, separated by a second fixed distance and with said fluid therebetween, wherein said second transmitter and said second receiver are configured at a non-perpendicular angle to flow of said fluid;

transmitting a second pulse from said second transmitter;

receiving said second pulse across said second fixed distance to create a second receiver signal;

creating a second trigger signal;

using said second trigger signal to transmit a repeat pulse from said second transmitter;

determining the signal delay between said transmitting and said receiving; and determining the transit-time shift between said second transmitter and said second receiver.

39. A method of controlling a dynamic fluid-supply system according to claim 38, wherein said first transmitter and said second transmitter are an integral unit.

40. A method of controlling a dynamic fluid-supply system according to claim 38, wherein transmitting comprises generating an audio signal in a frequency range from about 100 kHz to about 10 MHz, wherein said first pulse and said second pulse experience an attenuation between said transmitter and said receiver in excess of about 50%, wherein said first pulse and said second pulse each have an initial pulse width in a range from about 0.1 microseconds to about 5 microseconds, wherein said receiver signal is amplified for a gain between about 100 and about 10,000, wherein said receiver signal is converted into a square wave trigger signal with a width of about 10 microseconds, wherein said second pulse is generated from a source that has a potential in a range from about 60 volts to about 220 volts, and wherein elapsed time between said first pulse and second pulse is measurable in a range from about 0.1 kHz to about 100 kHz.

41. A method suitable for determining at least one flow parameter of a fluid having a direction of flow, the method comprising:

transmitting a first pulse through at least a portion of the fluid and across a first known distance, said first pulse traveling in a first orientation with respect to the direction of flow;

receiving said first pulse;

transmitting a second pulse through at least a portion of the fluid and across a second known distance, said second pulse traveling in second orientation with respect to the direction of flow;

receiving said second pulse;

measuring a Doppler shift between said first pulse and said second pulse; and determining a velocity of the flow based at least in part upon said Doppler shift.

42. The method as recited in claim 41, wherein said transmitting a first pulse through at least a portion of the fluid and across a first known distance, said first pulse traveling in a first orientation with respect to the direction of flow comprises transmitting a first pulse through at least a portion of the fluid and across a first known distance, said first pulse traveling in a direction substantially perpendicular to the direction of flow.

43. The method as recited in claim 41, wherein said transmitting a second pulse through at least a portion of the fluid and across a second known distance, said second pulse traveling in second orientation with respect to the direction of flow comprises transmitting a second pulse through at least a portion of the fluid and across a second known distance, said second pulse traveling in a direction oblique to the direction of flow.

44. The method as recited in claim 41, further comprising correlating said velocity of the flow to a percentage of solids present in the flow.

45. The method as recited in claim 41, wherein measuring a Doppler shift facilitates determination of velocities of said first and second pulses.

46. The method as recited in claim 45, wherein determining a velocity of the flow based at least in part upon said Doppler shift comprises calculating a difference between said velocities of said first and second pulses and using said difference to facilitate determination of said velocity of the flow.

47. The method as recited in claim 41, wherein determining a velocity of the flow based at least in part upon said Doppler shift is achieved using the equation:

$$= \frac{(d_1 J_1 - d_0 J_0)}{\cos(\Theta_1)}$$

wherein,
$V_f$ is said velocity of the flow;
$d_0$ is said first known distance;
$d_1$ is said second known distance;
$f_0$ is a frequency of said first pulse;
$f_1$ is a frequency of said second pulse; and
cosine $\Theta_1$ is a cosine of an angle cooperatively defined by said second orientation and the direction of flow of the fluid.

48. The method as recited in claim 41, wherein at least one of said first pulse and said second pulse is in a frequency range of about 100 kHz to about 10 mHz.

49. The method as recited in claim 41, wherein at least one of said first pulse and said second pulse has a frequency of about 1 mHz.

50. The method as recited in claim 41, wherein at least one of said first pulse and said second pulse has an initial pulse width in a range of about 0.1 microseconds to about 5.0 microseconds.

51. The method as recited in claim 41, wherein at least one of said first pulse and said second pulse has a potential in a range of about 60 volts to about 220 volts.

52. In a fluid system including a conduit through which a fluid flows, a method suitable for managing flow in the fluid system, the method comprising:
transmitting a first pulse through at least a portion of the fluid and across a first known distance, said first pulse traveling in a first orientation with respect to the direction of flow;
receiving said first pulse;
transmitting a second pulse through at least a portion of the fluid and across a second known distance, said second pulse traveling in second orientation with respect to the direction of flow;
receiving said second pulse;
measuring a Doppler shift between said first pulse and said second pulse; and determining a velocity of the flow based at least in part upon said Doppler shift;
comparing said velocity of the flow to a set-point velocity; and
optionally adjusting at least said velocity of the flow.

53. The method as recited in claim 52, wherein said first orientation comprises a direction substantially perpendicular to the direction of flow.

54. The method as recited in claim 52, wherein said second orientation comprises a direction oblique to the direction of flow.

55. The method as recited in claim 52, wherein measuring a Doppler shift facilitates determination of velocities of said first and second pulses.

56. The method as recited in claim 55, wherein determining a velocity of the flow based at least in part upon said Doppler shift comprises calculating a difference between said velocities of said first and second pulses and using said difference to facilitate determination of said velocity of the flow.

57. The method as recited in claim 52, wherein determining a velocity of the flow based at least in part upon said Doppler shift is achieved using the equation:

$$= \frac{(d_1 J_1 - d_0 J_0)}{\cos(\Theta_1)}$$

wherein,
$V_f$ is said velocity of the flow;
$d_0$ is said first known distance;
$d_1$ is said second known distance;
$f_0$ is a frequency of said first pulse;
$f_1$ is a frequency of said second pulse; and
cosine $\Theta_1$ is a cosine of an angle cooperatively defined by said second orientation and the direction of flow of the fluid.

58. A method suitable for determining the percent solids in a slurry containing a solid portion and a fluid portion, the method comprising:
generating a pulse;
transmitting said pulse through at least a portion of the slurry and across a first known distance;
calculating a velocity of said pulse; and
correlating said velocity to a percentage of solids present in said slurry.

59. The method as recited in claim 58, wherein correlating said velocity to a percentage of solids present in said slurry comprises estimating a speed of sound through the fluid portion of said slurry.

60. The method as recited in claim 58, further comprising determining a flow velocity of the slurry.

* * * * *